United States Patent
Tcholakian et al.

[19]

[11] Patent Number: 5,820,607
[45] Date of Patent: Oct. 13, 1998

[54] MULTIPURPOSE ANTI-MICROBIAL SILASTIC SHEATH SYSTEM FOR THE PREVENTION OF DEVICE-RELATED INFECTIONS

[75] Inventors: Robert Tcholakian; Issam Raad, both of Houston, Tex.

[73] Assignee: Board of Regents, University of Texas Systems, Austin, Tex.

[21] Appl. No.: 465,587

[22] Filed: Jun. 5, 1995

[51] Int. Cl.⁶ .................................................. A61M 5/32
[52] U.S. Cl. ............................ 604/265; 604/49; 604/54; 604/280
[58] Field of Search ................... 604/890.1, 265, 604/264, 280, 49

[56] References Cited

U.S. PATENT DOCUMENTS

| | | | |
|---|---|---|---|
| 3,566,874 | 3/1971 | Shepherd et al. | 128/349 |
| 3,598,127 | 8/1971 | Wepsic | 128/349 |
| 4,623,329 | 11/1986 | Drobish et al. | |
| 4,677,143 | 6/1987 | Laurin et al. | 523/122 |
| 4,925,668 | 5/1990 | Khan et al. | 424/422 |
| 4,994,047 | 2/1991 | Walker et al. | |
| 4,999,210 | 3/1991 | Solomon et al. | 427/2 |
| 5,041,100 | 8/1991 | Rowland et al. | 604/265 |
| 5,217,493 | 6/1993 | Raad et al. | 623/11 |
| 5,324,275 | 6/1994 | Raad et al. | 604/265 |
| 5,362,754 | 11/1994 | Raad et al. | 514/566 |

FOREIGN PATENT DOCUMENTS

| | | |
|---|---|---|
| 467516 | 1/1992 | European Pat. Off. |
| 9110466 | 7/1991 | WIPO |

OTHER PUBLICATIONS

Durand et al., "Characterization of Antigen Receptor Response Elements within the Interleukin–2 Enhancer," *Molecular and Cellular Biology*, 8(2):1715–1724, Apr. 1988.

Owaki et al., "Raf–1 is Required for T Cell IL2 Production," *The EMBO Journal*, 12(11):4367–4373, 1993.

Schierholz et al., "In Vitro Efficacy of an Antibiotic Releasing Silicone Ventricle Catheter to Prevent Shunt Infection," *Biomaterial*, 15(12):996–1000, Oct. 1994.

Sheretz et al., "Efficacy of Antibiotic–Coated Catheters in Preventing Subcutaneous *Staphylococcus aureus* Infection in Rabbits," *The Journal of Infectious Diseases*, 167:98–106, 1993.

*Primary Examiner*—Mark Bockelman
*Attorney, Agent, or Firm*—Arnold, White and Durkee

[57] ABSTRACT

The present invention relates generally to indwelling medical devices. In particular, there is provided a device constructed from permeable or nonpermeable material having a pharmacologically active ingredient layer surrounding the device, and an outer sheath which is permeable to the pharmacologically active ingredient. This construction provides a device that allows the pharmacologically active ingredient located between the catheter tube and the outer sheath to slowly diffuse through the outer sheath and/or inner tube, thus inhibiting microbial infection on the outer surface and lumen of the catheter.

34 Claims, 6 Drawing Sheets

MULTIPURPOSE ANTI-MICROBIAL SILASTIC SHEATH SYSTEM FOR THE PREVENTION OF DEVICE-RELATED INFECTIONS

FIELD OF THE INVENTION

The present invention relates generally to the field of medical devices. One particular application concerns catheters with pharmacologically active ingredients layered between the lumen and external surfaces of the catheter, including their application and preparation. The invention also concerns the field of long-term infection control in medical devices, as the described devices possess extended antimicrobial activity and hence, extended capacity to prevent/inhibit infection.

DESCRIPTION OF THE RELATED ART

Catheters used for vascular access, both arterial and venous, urethral, abdominal cavity tubing, drainage bags and various connectors are common sources of infection. In particular, a high percentage of patients who require long-term urinary catheters develop chronic urinary tract infections, frequently in conjunction with episodes of fever, chills and flank pain. Such patients are at risk of developing bacteremia or chronic pyelonephritis, conditions of high morbidity and mortality. Thus, a desirable feature of urinary catheters is that they should provide some means of infection control.

One way to control bacterial infections is by providing, concurrent with the catheter treatment, an antibiotic regimen. In addition to providing antimicrobial agents to combat catheter-related infections, it is sometimes desirable to deliver other agents such as anticoagulants and antifibins as adjuncts to the antimicrobial agents to prevent thrombotic occlusions and microbial colonization on both the external and luminal surfaces.

It is further desired that delivery of these pharmacologically active ingredients be maintained for a long duration of time, released in a relatively slow manner, and that the delivery be circumferential with the catheter or device rather than concentrated in particular areas. It is even further desired that the incorporation of the pharmacologically active ingredients in a delivery system as described can be adapted to all catheters ranging from simple to complex ones, and from adult to pediatric sizes. This also includes the various medical devices this technology can advance.

Some attempts have been made to incorporate an antimicrobial delivery system into a catheter, including those directed to adhering a pharmacologically active ingredient to the catheter itself. Laurin et al., U.S. Pat. No. 4,677,143, relates to the application of a coating of an antimicrobial agent mixed with a resin to the exterior of medical device, such as a catheter.

The problem with surface bonding is that it is limited to short-term delivery of the pharmacologically active ingredient. This residual antimicrobial activity after catheter removal (Table 1, step F) was demonstrated in detail in FIG. 12. The antimicrobials used were minocycline/Rifampin (2:1). After plating the catheters (as FIG. 2 and prototype 2) with silicone embedded antimicrobial jacket in ajar (as per Table 1), the catheters were reimplanted after each 7-day cycle and the used plates, where the catheters used to be, were kept and observed (Table 1, step F) to determine whether the residual antimicrobial agents released when the catheter was implanted in the ajar will still inhibit bacterial recolonization of the zone of inhibition in the absence of the catheter. FIG. 12 shows that the antimicrobial agents released from the catheter when present prevented recolonization of the zone of inhibition for up to 90+ days. This is because the surfactants used to facilitate bonding between the pharmacologically active ingredient and the catheter, such as tridodoecl-methylammonium chloride (TIDMAC) or benzalkonium chloride, have limited effectiveness due to their short binding duration. Furthermore, the direct contact between these pharmacologically active ingredients with biological fluids in such devices facilitates rapid depletion of the active ingredients.

Wepsic et al., U.S. Pat. No. 3,598,127 relates to an antibacterial agent placed as a powder in longitudinal grooves between the catheter wall and a polysiloxane rubber layer. The polysiloxane layer was permeable to the antibacterial agent, allowing the agent to diffuse through the layer. The Wepsic et al. patent used longitudinally spaced grooves to contain the powdered bacterial agent. This is believed to be an undesirable and less effective arrangement, as it does not result in even diffusion around the circumference of the catheter or prolong the antimicrobial activity of the catheter beyond that of the surface coated catheters. Furthermore, the presence of the powder makes it very difficult to manufacture this design and reproduce a unit that consistently produces reproducible results. This is due in part to the uncontrolled powder concentration in the grooves.

Although others have addressed the problem of incorporating a delivery system for pharmacologically active ingredients in a catheter, satisfactory solutions have not yet been achieved. The present invention is directed to providing such a solution.

SUMMARY OF THE INVENTION

The present invention seeks to overcome these and other drawbacks inherent in the prior art by providing a device that is surrounded with a layer of pharmacologically active ingredient which, in turn, is surrounded by an outer sheath composed of silicone. This layer is permeable to the pharmacologically active ingredients, yet provides a safety barrier between the pharmacologically active ingredients embedded in the device and the surrounding biological fluids. The devices of the present invention also provide the advantage of allowing diffusion of the pharmacologically active ingredient both into the lumen of the device and outward to the exterior surface of the device.

In one embodiment, the present invention comprises an indwelling medical device having an elongated, hollow lumen, providing an inner shell to the device. This inner shell is surrounded by selected pharmacologically active ingredients. These ingredients may either be suspended in, for example, silicone, or take the form of a powder layer. These pharmacologically active ingredients, in turn, are surrounded by an outer solid sheath of silicone, or other pharmacological-agent permeable material. The ingredients may thus slowly diffuse through the inner sheath and/or outer sheath. The diffusion of the pharmacologically active ingredients through the outer sheath provides a circumferential layer on the surface of the device to inhibit microbial colonization. In some embodiments, the outer sheath is constructed from polysiloxane rubber. Other materials may, however, be used as long as they are biologically inert. Both materials that allow for the diffusion of pharmacologically active ingredients (having a molecular weight less than or about 2,000 kDa), may be used in conjunction with the invention, selection depending primarily on the desired use of the device.

An alternative embodiment of the present invention uses a jacket of silicone impregnated with at least one pharmacologically active ingredient as a sandwiched layer between the inner surface that surrounds the lumen, and the external layer comprising the sheath, in lieu of a "sandwiched" crystalline layer of pharmacologically active ingredient.

Thus, the present invention provides an indwelling medical device which incorporates a system for delivering pharmacologically active ingredients in a slow, controlled manner over a long duration of time. In addition, pharmacologically active ingredients are evenly distributed around the entire circumference of the device.

The present invention may be adapted to all indwelling medical devices, and existing devices may be modified to contain the delivery system described by the present invention.

The construction of the antimicrobial jacket and surrounding outer sheath, although are described for catheters, they can apply to any medically implantable device.

Furthermore, the devices of the invention do not have to be constructed from permeable material, but may in some embodiments be constructed of semi-permeable materials, or a combination of both permeable and semi-permeable materials. Some embodiments of the device may be comprised of material that is less permeable than silicone, or not permeable at all, to the particular pharmacologically active agent used, yet the device can be surfaced with an antimicrobial agent bonded with silicone and covered with a silicone sheath. Such semi-permeable or non-permeable device materials include teflon, polyurethane, carbothane, polyethylene, tigan and various other plastic materials used in medical devices.

The device of the invention may be fashioned to provide any variety of catheter desired, whether the catheters are constructed from permeable, semi-permeable or non-permeable materials. If drug diffusion is desired into both the lumen of the catheter and to the surface of the catheter, the catheter tube material selected should at least be semi-permeable to the pharmacologically active agent selected. If drug diffusion is desired to the surface of the catheter or device, such catheter tube or device material can be constructed from the various non-permeable plastics used in medical devices.

Generally stated, in most embodiments of the invention, the pharmacologically active substances of the catheter diffuse through the outer sheath and surround the outer circumference or surface of the catheter, thus providing a protective zone of antimicrobials. Where the inner jacket/coating of the catheter lumen is of a permeable or semi-permeable material, the antimicrobial will also diffuse into the lumen of the catheter, thus providing still further anti-infection control and suppression of intrapumenal colonization of bacteria.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Indwelling Medical Devices

Medical devices according to the present invention include any such devices that are indwelling in a patient or animal. Such devices include abdominal cavity drainage bags, connectors and tubing used by colostomy patients. Angioplasty devices also are included within the present invention. Preferred devices are catheters in including introducing, sensing and monitoring catheters. More preferred are urinary, venous, arterial, and peritoneal catheters, tracheotomy devices, shunts and other medical devices or prosthesis.

Figure 1:
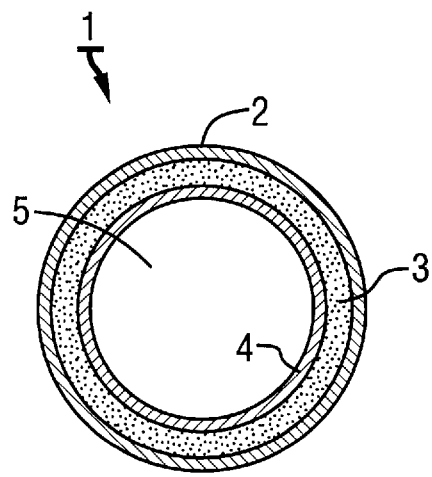
FIG. 1 is a cross section of a catheter (1) according to the invention having a silicone sheath jacket on the exterior surface (2) with a pharmacologically active antimicrobial agent (crystalline form) (3) sandwiched by an inner (luminal) layer of silastic (4) that forms the lumen of the catheter (5).
Figure 3:
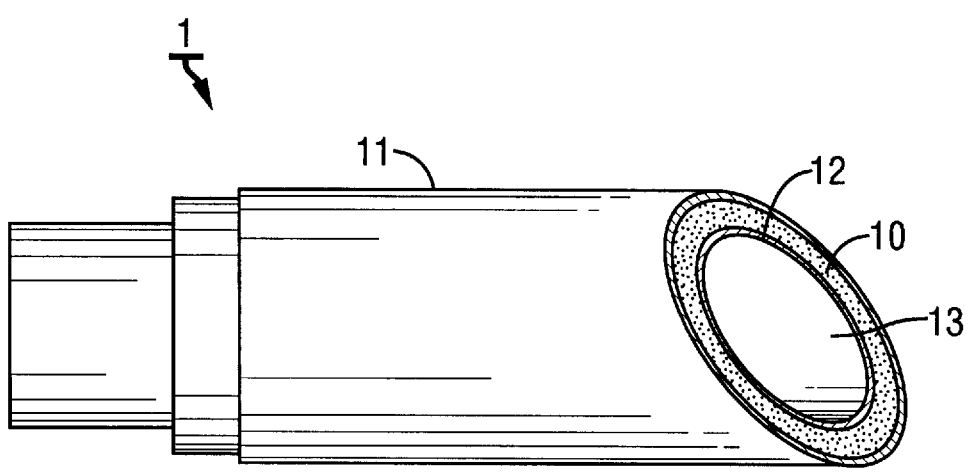
FIG. 3 is a longitudinal cutaway of a catheter according to the present invention which contains a silicone jacket impregnated with a pharmacologically active ingredient (10), covered with an outer surface silicone sheath (11). Cutaway also shows inner luminal sheath (12).

With reference to FIGS. 1 and 3, a catheter (1), according to one version of the present invention, comprises a catheter lumen (5) defining a hollow fluid passage through which fluids may be administered or withdrawn from the patient. The catheter (1) being surrounded by a layer (3), of pharmacologically active agents. These pharmacologically active ingredient may be in crystalline form. The layer (3) is, in turn, surrounded by an outer sheath (2). This outer sheath (2) is in some embodiments at least partially permeable to the pharmacologically active agents. The permeability of the sheath (2) allows the pharmacologically active agents to diffuse out from the layer (3) and through the outer sheath (2) and eventually to surround the outer circumference of the catheter. The catheter (1) may be any standard catheter which is currently available. It is desirable that the catheter (1) be made of silicone or a like at least semi-permeable material when it is desirable for the pharmacological agents in layer (3) to also diffuse into the lumen of the catheter (5).

In some embodiments, the outer sheath (2) is constructed from a material which is at least partially permeable to the pharmacologically active agents in layer 3. The material used and the thickness of the outer sheath (2) will determine how rapidly the pharmacologically active ingredient will diffuse through the outer sheath (2) and into the surrounding environment. Thus, the selection of material for the outer sheath (2) will depend upon the particular application.

Figure 4:
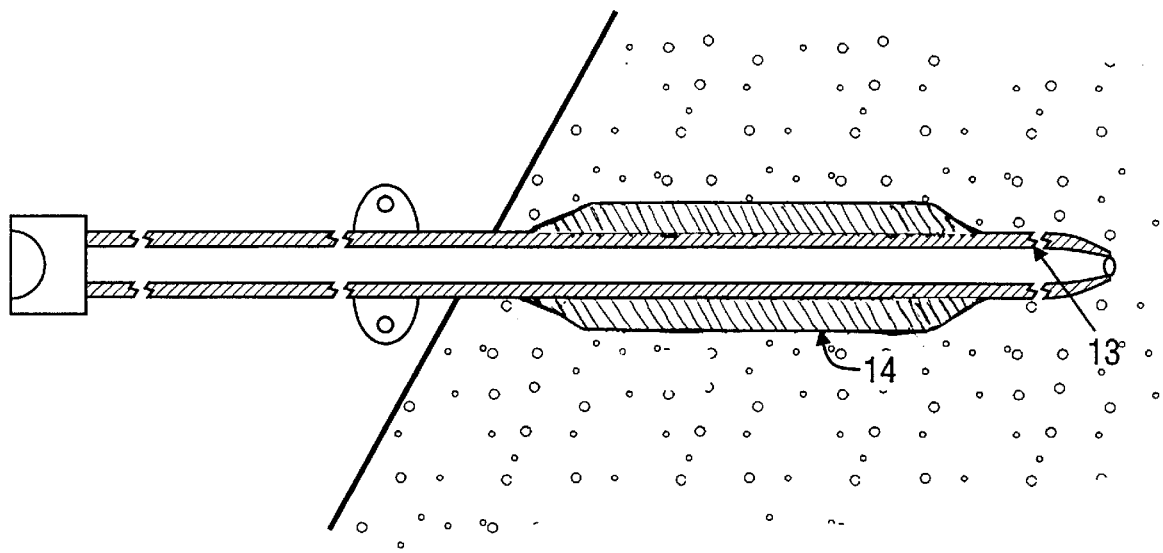
FIG. 4 is a longitudinal section of a catheter according to the present invention having a layer of pharmacologically active ingredients (13) and an outer sheath (14) which does not extend for the full length of the catheter.
Figure 5:
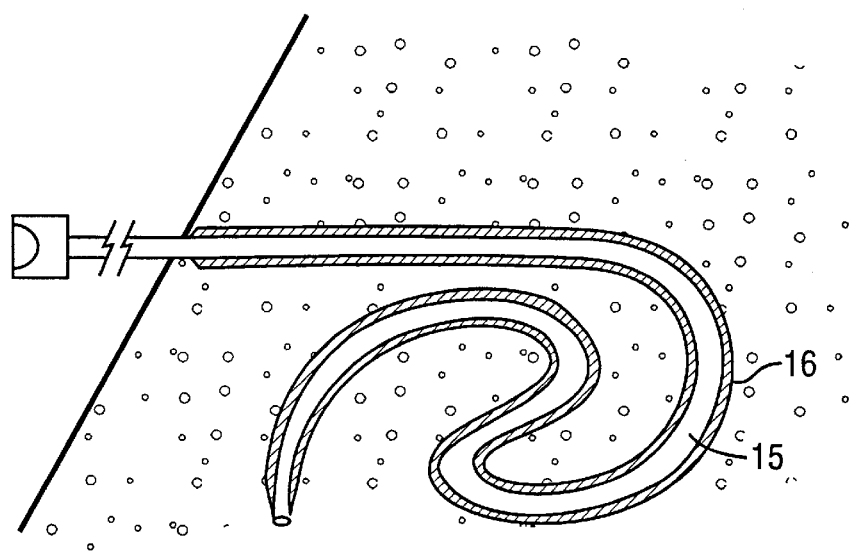
FIG. 5 is a longitudinal section of a catheter according to the present invention having a layer of pharmacologically active ingredients (15) and an outer sheath (16) coextensive with the length of the catheter.

The layer of pharmacologically active ingredients (15) and the outer sheath (16) may be coextensive with the underlying catheter (1) extending the entire length of the catheter as depicted in FIG. 5, or alternatively, may be limited to a portion of the catheter (1) which is in direct contact with the surrounding tissue, as depicted in FIG. 4.

Figure 2:
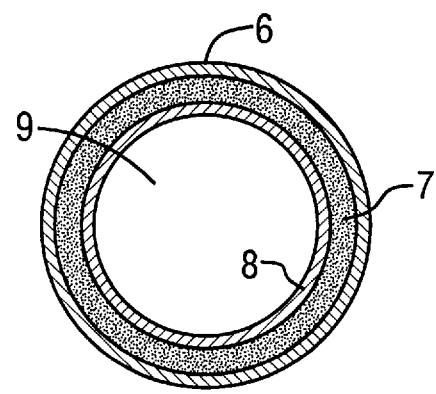
FIG. 2 is a cross section of a catheter according to the present invention having a silastic sheath jacket on the exterior surface (6) with a pharmacologically active antimicrobial agent totally embedded in silicone to form layer (7) sandwiched by an inner (luminal) layer of silicone (i.e., an inner sheath) (8) that surrounds the lumen of the catheter (9).

An important alternative to using layer (3) in FIG. 1 is depicted in FIG. 2. In this embodiment, the catheter (1) is surrounded by a layer of pharmacologically active ingredient embedded in a silicone jacket (7), which in turn is surrounded by an outer silicone sheath (6). The catheter (1) and outer sheath (6) serve to sandwich the pharmacologically active ingredient (7) as an integral part of the catheter construction. As in the previous embodiment, the concentration of the pharmacologically active ingredient, its density when embedded in the silicone (7) and the thickness of the outer sheath (6) will determine the rate at which the pharmacologically active ingredient in the silicone jacket (7) will diffuse through the outer sheath (6) and surround the surface of the catheter. Thus, the selection of the outer sheath (6) material will vary depending on the specific application. Again, it is preferred for the inner sheath surrounding the lumen of the catheter or the surface of the device to be made of silicone or similarly permeable or semi-permeable material if it is desirable for the pharmacological agents in the middle layer (7) to diffuse into the lumen (9) of the device.

In the previous embodiment, the layer of the pharmacologically active ingredient (15) and the outer sheath (16) may be coextensive with the catheter as depicted in FIG. 5 or may be limited in length to the area most directly in contact with the surrounding environment, such as a tissue, as depicted in FIG. 4.

B. Pharmacologically Active Ingredients

Any pharmacologically active ingredients may be used in preparing the devices of the present invention. Typical pharmacologically active ingredients include anticoagulants, antifibrin agents, antiinflammatory agents and antimicrobials. Anticoagulants included EGTA, EDTA, heparin, urokinase, streptokinase, and others. Antiinflammatory agents include steroids, nonsteroidal antiinflammatory agents, and salicylates.

Antimicrobials include antibiotics antifungal and antiviral agents. Antibiotics include minocycline, rifampin, penicillins, cephaloporins, monobactams, carbapenems, clindamycin, chloramphenicol, tetracycline, quinolones, macrolides, sulfa antibiotics, trimethoprim, fusidic acid and aminoglycosides. Antiviral agents include acyclovir, ganciclovir, fosiornet and pencyclovir. Antifungal agents include amphotericin B, azoles, flucytosine, cilofungin and nikko Z.

In certain applications, it will be sufficient to provide a single pharmacologically active ingredient in the device. In other situations, it will be desirable to combine compatible ingredients. For example, it may prove useful to provide an antimicrobial agent along with an anticoagulant and/or an antiinflammatory agent. In another example, it may prove useful to provide multiple antimicrobial agents with differing target specificities, modes of action or duration together either alone or together with anticoagulants or antiinflammatory agents.

C. Outer Sheath and Antimicrobial Jacket Materials

The composition and thickness of the outer sheath and, in certain embodiments the jacket, will help determine how rapidly the pharmacologically active ingredient is released from its silicone matrix, through the outer sheath and for what period of time the pharmacologically active ingredient will continue to be released. It is contemplated that the sheath will be from 0.1 to 3 millimeters in thickness, preferably 0.2 to 0.4 mm. The jacket will range from 0.1 to 3 millimeters in thickness, preferably about 1 to about 2 mm, and in other embodiments, about 1.59 mm (actual size of jacket).

It is contemplated that the sheath will be from 0.1 mm to 1.5 mm in thickness, preferably 0.15 mm to 0.25 mm. The jacket will range from 0.1 mm to 3.0 mm in thickness, preferably 0.20 mm to 0.30 mm. The prototype catheter had a sheath that was prepared so as to have a thickness of about a 0.2 mm thickness for the inner luminal layer, middle jacket layer, and outer sheath, (middle jacket layer containing the pharmacologically active agents). In these embodiments, the pharmacologically active ingredient(s) is embedded in the silicone.

The outer sheath/jacket may, but need not be, made of the same material as the inner sheath that surrounds the catheter lumen. Suitable materials for the sheath and jacket include various silicone formulas. It has been found that polysiloxane rubber is useful in many applications. Polysiloxane materials are available commercially, and are known by the trade name SILASTIC (Dow Corning, Midland, Mich.; Baxter, McGaw Park, Ill.).

D. Diffusion Kinetics

The rate of release for the pharmacologically active ingredient is inversely proportional to the duration of release. Depending on the clinical situation, the desired amount of ingredient released per unit of time will vary, as will the desired duration of release. For example, where the likelihood of infection is high, a correspondingly high level of antimicrobial release may be desired. Similarly, if the device will be in contact with the patient for only a short period of time, a high rate of release (and short duration) is acceptable. In circumstances where the patient is sensitive to higher levels of the pharmacologically active ingredient, or where the device is in contact with the patient for an extended period of time, a lower release rate may be preferred.

One factor affecting duration of release is the initial concentration of pharmacologically active ingredient in the device. Typically, the higher the initial concentration of the pharmacologically active agent, the longer the duration of release of the agent will be. The release rate is affected by the thickness of the outer sheath and the density of the materials used to construct the antimicrobial jacket, as discussed above.

It is well within the skill of those in the field to alter release rates in a variety of different ways. For example, it is possible to produce a delayed release profile, where little or no pharmacologically active ingredient is released initially, while allowing, after a predetermined period, substantial release of the included pharmacologically active ingredient. It also is possible to obtain "burst" release profiles, where the ingredient is delivered in concentrated bursts over an extended period. In still other embodiments, the device starts acting to release the pharmacologically active agent beginning at the time of insertion. Similarly, it is possible to produce stable, continuous levels of release over the same, extended periods.

Contemplated release periods range from one minute to weeks and even months. The appropriate levels of release for given pharmacologically active ingredients may be determined by reference to standard medicinal formularies.

E. Preparation of an Antimicrobial-Containing Catheter

All of the compositions and methods disclosed and claimed herein can be made and executed without undue experimentation in light of the present disclosure. While the compositions and methods of this invention are described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein, while the same or similar results would be achieved. All such similar substitutes and modifications apparent to those skilled in the art are deemed to be within the spirit, scope and concept of the invention as defined by the appended claims. The following examples are illustrative of the present invention but should not be considered, in any way, to be limiting.

EXAMPLE 1

Construction of a "Sandwich" Catheter Prototype
Preparation of the Original Sheath Prototypes The present example demonstrates the methods that were used in the preparation of two prototypes of the sheath catheter.

These prototypes were constructed from 3 cm segments of silastic tubing. Two types were made. The first type was made with micronized pharmacologic agents (crystalline powder) packed between two concentric silastic tubes. The second type was made from micronized pharmacologic agents compounded with clear RTV sealant silicone, and embedded as a sandwich between an outer layer (sheath) and an inner luminal layer of clear RTV sealant silicone layers.

The first type is similar to the cross-section shown in FIG. 1.

The second type is similar to the cross-section shown in FIG. 2.

The silastic tubing used for preparing the prototypes was Medical Grade Tubing (Dow Corning Silastic ®Brand, Cat No. 602-305). Other tubing used included a "Silicone Tubing" (Baxter, S/P™ Medical Grade, Cat T5715; McGaw Park, Ill.). The sealant used in preparing the devices was the 732™ Multipurpose Sealant, a 100% silicone rubber (Dow Corning®, Midland, Mich.). This material was used to seal the ends of the catheters as shown in FIG. 1. This silicone was also used to prepare the antimicrobial jacket layer (7) in FIG. 2, and was used to mold the sheath (6) and the lumen (8) layers of the catheter structure.

PROTOTYPE I

Two different sizes of "Silastic" Brand (Dow Corning) tubes were used. The tube sizes were:
 tube 1—(larger tube) 3.175 mm O.D./1.981 mm I.D.
 tube 2—(smaller tube) 1.7 mm O.D./0.8 mm I.D.

The outer sheath had a thickness of about 1.194 mm (3.175−1.981=1.194). The jacket layer containing the pharmacologically active agents had a thickness of about 0.28 mm (1.981−1.7=0.281 mm). The inner luminal layer had a thickness of about 0.9 mm (1.7−0.8=0.9 mm).

Step 1: Tube 2 is slipped into tube 1. One end of the double tube was plugged with the silicone sealant, RTV 732 (Dow Corning, Midland, Mich.).
 Step 2: A pocket or layer was formed between tube 1 and 2. This space was packed with micronized pharmacologic agent, minocycline, rifampin, minocycline/rifampin, minocycline/EDTA, EDTA, Fusidic acid, gentamycin, aztreonam, minocycline/aztreonam.
 Step 3: When the segment is filled with the pharmacologic agent, the open end of the segment was sealed in the space between tubes 1 and 2.

Two types of sealants were used, these were:
 1. silastic medical adhesive type A (Dow Corning, Cat No. 891); and
 2. RTV Sealant No. 732 (Dow Corning Corporation Medical Products—Midland, Mich. 48640)

Several of these prototypes were produced using different pharmacologic agents, minocycline, rifampin, minocycline/rifampin, minocycline/EDTA, EDTA, Fusidic acid, gentamycin, aztreonam, minocycline/aztreonam.

PROTOTYPE 2

The second prototype produced is demonstrated in FIG. 2. The pharmacologically active agent is compounded in a silicone matrix. This combination of silicone and pharmacological agent was used to provide a layer around the tube as described below. Also, the most preferred pharmacological agents used were minocycline/rifampin and minocycline.

This catheter was made in two different steps:
 Step 1: A pharmacologic agent-containing silicone was fashioned like a jacket around the silastic tube.
 Step 2: A silicone sheath was molded over the pharmacologically agent-containing jacket of step 1.

Each time a catheter was made, two different size molds were used. One was used to fashion the jacket containing the pharmacologically active agent over the silastic tube and a larger size mold was then used to construct the silicone sheath over the jacket containing the pharmacologic agent.

The bores in the molds used to prepare the device were precisely drilled to specification, honed and polished in order to prevent the silicone from adhering to it.

Steps in Building Prototype II

Step 1. A small silastic tube (0.8 mm I.D./1.7 mm O.D.) was used as the central luminal portion of the catheter.

Step 2. A mold with bore size 2.77 mm was used most often to form the jacket layer of material containing the pharmacologically active agents (i.e., antimicrobial agents).

Step 3. Preparation of the pharmacologically active agent containing material: Micronized minocycline/rifampin (2:1) in a concentration of 120 mg minocycline and 60 mg rifampin per gram of RTV silicone 732 sealant were mixed thoroughly. This mixture was spread into the bore surfaces of both halves of the mold.

Step 4. The silastic tube in Step 1 (1.7 mm O.D.) was pressed and aligned central in the bore of the mold and both mold surfaces pressed together with a vice or clamp.

Step 5. After catalysis was complete (about 30 min.), the mold halves were pried apart and the catheter was released. The catheter now included a jacket of the pharmacologically active ingredient bonded to the silastic tubing.

Step 6. Excess material was trimmed from the jacket surface.

Step 7. A mold with bore size 2.95 mm was used and RTV silicone 732 was spread into the bore surfaces of both halves of the mold.

Step 8. The jacket of Step 5 containing the pharmacologically active agents was centrally placed in the bore of the mold containing the RTV sealant (prepared in Step 7) and the mold halves pressed together with a vice or clamp.

Step 9. After catalysis was complete (about 30 min.) the mold haves were pried apart and the completed catheter was released. The catheter now included a silicone sheath over the jacket containing the pharmacologically active agent.

Step 10. The excess material was trimmed from the catheter. The catheter was allowed to rest for several days to allow the catalytic products to dissipate before plating them. The outside diameter of the catheter was 2.95 mm. The outside sheath thickness was 0.18 mm (2.95−2.77=0.18 mm).

The above diameter sizes do not represent preferred or even typical dimensions of the catheters of the present invention. Moreover, the particular dimensions of the above prototypes are not considered the ideal sizes for manufacturing dimensions. The sizes were selected as representative only of standard dimensions for the present studies, and particularly for the studies conducted in the following examples, using the device as diagramed in FIG. 2.

EXAMPLE 2

Prototype System

The efficacy of the prototype catheter segment was established by determining its ability to inhibit microbial growth expressed as "zone of inhibition." The procedure involved sterilizing the catheters with ethylene oxide gas. *Staphylococcus epidermis* (SE-5667) was subcultured to a blood agar plate from frozen stock of SE-5667 (obtained from a patient with a blood strain infected with *S. epidermidis*).

Methods

To 1000 ml of Meuller Hinton agar, 5 ml of a 0.5 McFarland turbidity standard was added when the agar became cool to the touch. A small amount of agar was poured into each dish and allowed to harden. The sterilized silicone catheter as prepared in Example 1, prototype 2, was placed in the center of the dish and a small amount of agar was poured over it to partially cover the catheter. The agar was allowed to harden, then another portion of agar was poured over the catheter in an amount enough to completely cover the device. The plate was then incubated for 24 h at 35° C. Twenty-four hours later, the zone of inhibition (mm) of the *S. epidermidis* was measured and recorded. In some studies, the zone of inhibition was measured daily and on day seven. This 7-day period is referred to as one "cycle" of activity for purposes of describing the studies in the present invention.

On day seven, the catheter was removed from the original plate, wiped clean with an alcohol prep, the alcohol allowed to evaporate. The catheter was then reimplanted in a new agar plate prepared identically to the first cycle preparation above. The new 24 h zone of inhibition after reimplantation was again recorded, and daily measurements recorded thereafter. At the end of 14 days, the third cycle was started and the zones of inhibition were continually recorded until the zone was "0" (i.e., no evidence of anti-microbial activity), or until the plate could no longer be read. A summary of the method of use in determining the zone of inhibition is outlined in Table 1.

TABLE 1

DETERMINATION OF THE ZONE OF INHIBITION

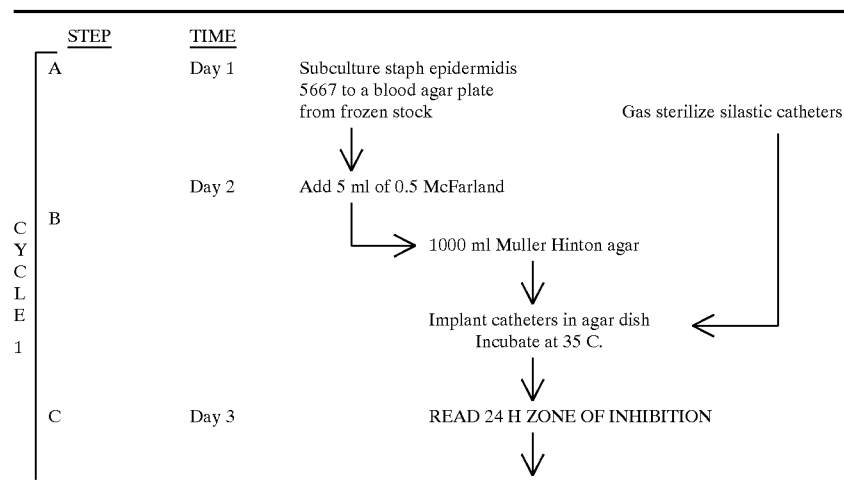

TABLE 1-continued

DETERMINATION OF THE ZONE OF INHIBITION

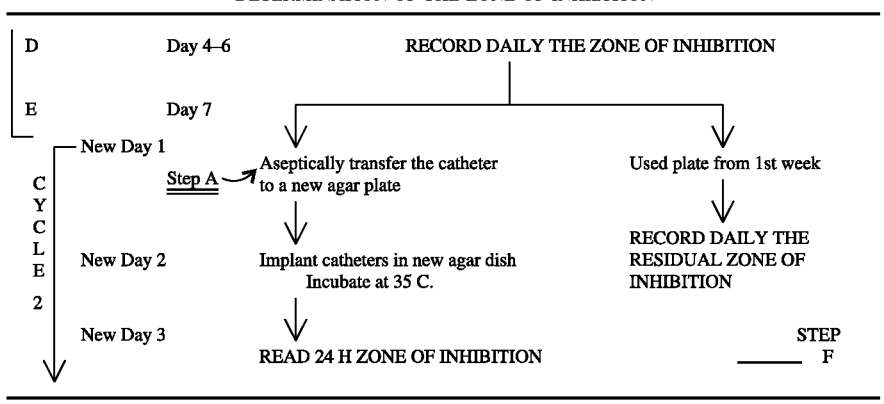

EXAMPLE 3

Antibiotic Effects of a "Sandwich" Catheter

The catheter used here is the same as FIG. 2 and prototype 2.

The present example demonstrates the anti-microbial activity observed with catheters that include the herein disclosed internal layer of pharmacologically active substances embedded in silicone and presented as a jacket sandwiched between two layers of silicone as demonstrated in FIG. 2.

Methods

Staphylococcus epidermis (SE) strain 5667 was subcultured to a blood agar plate (BAP) from a frozen stock as described in Example 2. Five to ten colonies of SE were subcloned into three 5 ml tubes and incubated for two hours. Three flasks of Muellar Hinton agar, 500 ml each, were prepared and autoclaved. After cooling, one of the 5 ml tubes was added to each of the Muellar Hinton agar flasks. The flasks were mixed gently by swirling, and a small amount of the infected agar was poured into petri dishes, enough to cover the bottom of the plates. After cooling for about fifteen minutes, sections of catheter were placed on the agar and a small amount of agar was poured on top of the catheter, enough to submerge the entire catheter. After cooling for about fifteen minutes, the plates were placed at 37° C. in an incubator for 24 hours. At seven day intervals, the catheters were removed and replaced according to the protocol outlined in Example 2 and Table 1.

Results

The submerged segments diffused the antimicrobial content along the entire circumferential surface of the sheath. The zones of inhibition observed were significant and continued to be so after multiple replatings of the same catheter segments. For example, after four replatings (FIG. 8), a silicone sheathed catheter containing minocycline and rifampin powder and embedded in silicone (FIG. 1 and FIG. 2), maintained a zone of inhibition of 35 mm. A zone of at least 15 mm has been correlated with in vivo efficacy[9]. In contrast, an Arrow Gard catheter coated with chlorhexidine gluconate and silver sulfadiazine, described in some clinical tests to reduce infection rates at least four-fold over untreated control[10], lost essentially all antimicrobial activity, and had a zone of inhibition of zero after two replatings. FIG. 9.

EXAMPLE 4

Construction of a Trilayer Catheter

The present example outlines the preparation of commercial embodiments of the invention. The 3 layers of the catheter will be extruded simultaneously, with all layers contributing to the catheter lining thickness and overall structural integrity. The various layers of these catheters are depicted in FIG. 2.

The two outermost layers, the outer sheath and middle antimicrobial jacket (FIG. 2: items 6,7), can be utilized in constructing any medical device or prosthesis to inhibit and/or prevent device-related infections. This is accomplished by bonding these layers to the surface of any device where such device is implanted and in contact with body fluids.

Methods

The catheter is to be extruded through an silicone extrusion machine, with the appropriate specialized tooling needed to force the antimicrobial components at a specified rate and thickness between the inner and outer silicone or other similarly permeable or semi-permeable layers of the device. This will produce a uniform internal "sandwiched" layer of the selected pharmacologically active agent (i.e., antimicrobial) throughout the device. The extrusion of the luminal tubes and the injection of the sheath is to occur in one single step. These three layers produce a sandwiched antimicrobial catheter (FIG. 2) with an interior lumen (9) surrounded by a silicone layer (8) and a middle jacket (7) and an exterior silicone sheath (6). The thicknesses of each layer is specified according to application and need.

Figure 11:
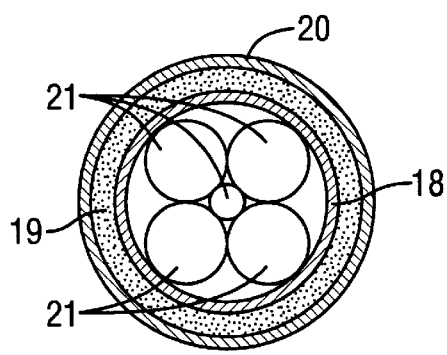
FIG. 11 shows a multi-lumen catheter that includes a single inner sheath (17) and a layer that includes a pharmacologically active ingredient (18) and an outer sheath (19). The drawing depicts a catheter device having five lumens (20).

After extrusion of the main body of the catheter, the "tubing" is to be cut at specified lengths and fitted with other standard structural components of an insertable device to form a usable unit prior to use. The "tubing" section is to be in some embodiments fitted with a silicone tip and a silicone-plastic manifold. Where multi luminal catheters are constructed (see FIG. 11), a multi-manifold unit is to be attached to the end of the pharmacological active agent/silicone coated tube to form a completed catheter ready for use.

Description and Materials Used to Construct Commercial Embodiments of the "Sandwich" Catheter 1. Silicone extrusion machines will be employed to extrude the catheter parts simultaneously as described herein.
2. Tooling devices that satisfy particular dimensional specifications for the desired catheter size will be used to manufacture the commercial products.
3. The pharmacologically active agent-containing silicone, prepared with powder crystalline forms of the agent, will be extruded through tooling devices as described in (2) using the silicone extrusion machines in (1), to provide a catheter layer within the device that is co-extensive with all or at least some portion of the length of the device.

4. Extrusion manufacture of the catheter tubing with its several layers will occur simultaneously, with the inner luminal layer, the middle "sandwiched" antimicrobial layer and the outer sheath layer being extruded at the same time.

5. The sandwich tubes in (4) above will then be cut into segments of desired lengths and fitted with a tip and a manifold part. The device will then be structurally ready for use. The tube containing a sandwiched layer of antimicrobial is in some embodiments to be fitted with a tip made of silicone.

6. The tube in (5) is in some embodiments to be then fitted with a silicone manifold, the injection parts being in particular embodiments constructed out of standard plastic manifold materials.

Construction of a Trilayer Catheter

The tri-layer catheter embodies a design and concept similar to the sandwiched catheter described in Example 1 and the sandwich catheter described above.

Layer 1—The innermost layer can consist of a single tube (i.e., single lumen) or multi-lumen tube with the limiting circumference preferably composed of silicone. In various other applications, the innermost layer can be any medical device or prosthesis requiring antimicrobial coatings to prevent device-related infections.

Layer 2—Layer 2 is the middle layer of the device, and comprises silicone and any variety of desired pharmacological agent(s). In one embodiment, the antimicrobial agents, are micronized and mixed homogeneously with the "A" and "B" components of the silicone preparation mixtures. The silicone mixture "A" and "B" are mixed together at extrusion, thus initiating the catalytic process that cures the silicone and solidifies the device structure. This form of mixing of the antimicrobials with equal concentration in A and in B components of the silicone, renders a final product with uniform essentially equal concentrations of components A and B. This produces an accurate concentration of antimicrobial per gram silicone. A relatively high concentration of antimicrobial agents for use in the invention is about 180 milligrams of antimicrobial/gram of silicone after extrusion. This concentration, of course, will vary from 75%, 50% or even 25%. The selection of particular amounts of the antimicrobial or other active agent in the device will depend upon the design of the catheter or device and its particular intended use.

Layer 3—Layer 3 in some embodiments of the catheter constitutes the outer-most layer or sheath encapsulating the antimicrobial layer described above. In some embodiments, this third layer is constructed of silicone. As already discussed, the thickness and the formulary type of silicone used to establish its density will determine in some embodiments the rate at which the antimicrobial agents in layer 2 diffuse out and around the circumference of the catheter or device. The variations in thickness and density of the silicone used for this layer are a matter of design choice, and will depend upon the intended use of the catheter or device.

Layers 1, 2, and 3 as described above are extruded simultaneously so as to form a single, solid integral unit with 3 inseparable layers. The second layer containing the antimicrobial agents or other pharmacological agents will occupy space and thus tend to increase the relative diameter of the catheter, and/or size of the device. Control of the overall diameter of the device is thus important to consider in particular intended applications for the device, such as for use as vascular catheters where smaller total diameters are desired.

The solid integration of the second layer also adds support and strength to the walls of the catheter or device, thus permitting one to minimize the thicknesses of layers 1 and 3 to compensate for the added strength and thickness of layer 2. This also enables a reduction of the thicknesses of the whole catheter wall so as to produce a catheter that is sufficiently similar in size so as to provide a device comparable to standard devices/catheters that lack the second and third layers, enhancing the ready usability of the presently disclosed devices.

The extruded tube composed of the trilayer catheter is to be cut at specific lengths and fitted with other standard catheter components, readily available, to form a useable unit, as already discussed.

EXAMPLE 5

Antibiotic Effects of a Trilayer Catheter

The antibiotic effects of catheters made according to Example 3 were evaluated in assays as described in Example 2.

The results were similar to those reported above, with catheter segments retaining their antibiotic activity after as many as four replatings. In addition, the antibiotic activity was observed to persist in the cultures for up to ninety days after removal of the catheter, without recolonization from surrounding flora (FIG. 12).

Figure 12:
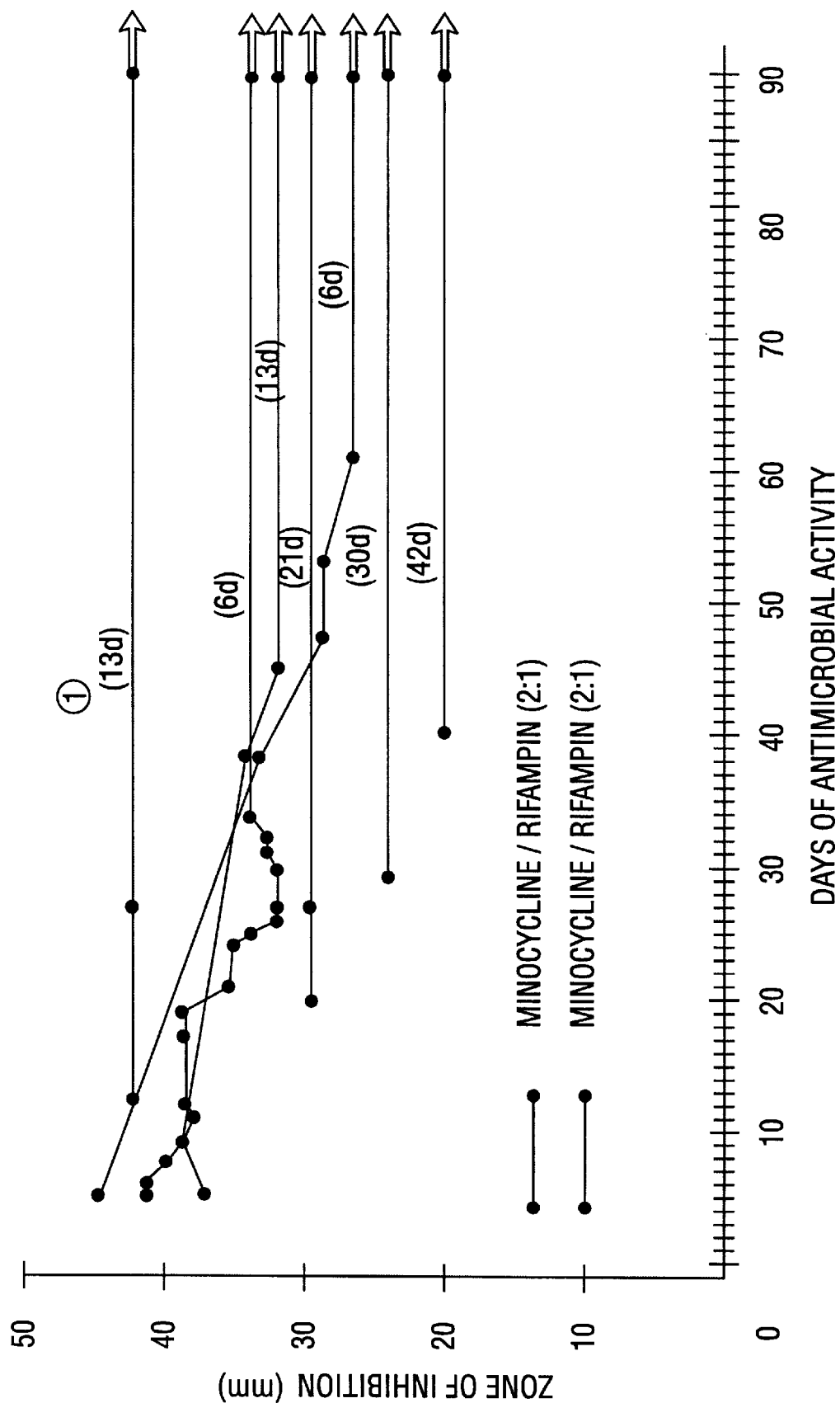
FIG. 12 (residual antimicrobial activity) shows antimicrobial activity after catheter removal. The indicated numbers (13d, 6d, 21d, 30d, 42d) refer to the day, measured in days, after the catheter had been removed from the agar in an initial test for antimicrobial activity.

This residual antimicrobial activity after catheter removal (Table 1, step F) was demonstrated in detail in FIG. 12. The antimicrobials used were minocycline/Rifampin (2:1). After plating the catheters (as FIG. 2 and prototype 2) with silicone embedded antimicrobial jacket in agar (as per Table 1), the catheters were reimplanted after each 7-day cycle and the used plates, where the catheters used to be, were kept and observed (Table 1, step F) to determine whether the residual antimicrobial agents released when the catheter was implanted in the agar will still inhibit bacterial recolonization of the zone of inhibition in the absence of the catheter. FIG. 12 shows that the antimicrobial agents released from the catheter when present prevented recolonization of the zone of inhibition for up to 90+ days.

EXAMPLE 6

The Effect of Various Sterilization Methods on Silicone Sheathed Antimicrobial Catheters The catheters were constructed as described in Example 1, prototype 2 (as shown in FIG. 2).

Figure 6:
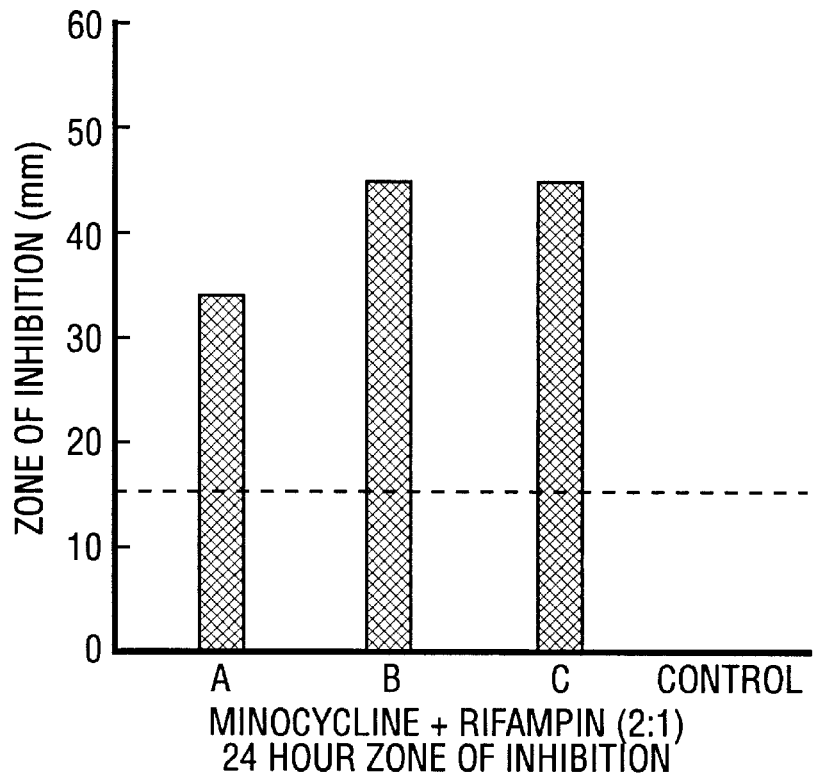
FIG. 6 demonstrates the effect of various sterilization methods on silicone sheathed antimicrobial (minocycline/rifampin; 2:1) inhibition. Zones of inhibition above 15 mm are considered as having significant antimicrobial activity. A=Gas Sterilization; B=Gamma Radiation Sterilized 2–3 Mega Rad; C=Ethanol-dip sterilization.
Figure 7:
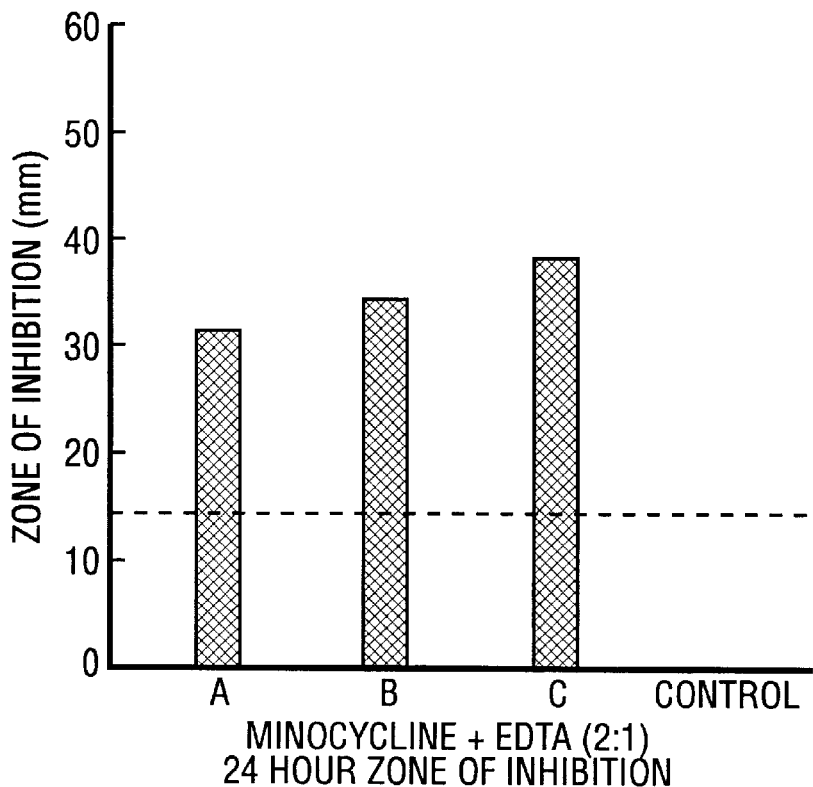
FIG. 7. shows the effect of various sterilization methods on silicone sheathed antimicrobial/anticoagulant (minocycline/EDTA; 2:1) catheters. A=Gas Sterilization; B=Gamma Radiation Sterilized 2–3 Mega Rad; C=Ethanol-dip sterilized.

The 24 h zones of inhibition post-sterilization were recorded as shown in FIG. 6 for catheters containing minocycline/rifampin (2:1:) and in FIG. 7 for catheters containing minocycline/EDTA (2:1).

The data indicates that no residual effects of sterilization affected the zones of inhibition. This is evidenced by the absence of any inhibition in the control samples. All the forms (gas sterilization, gamma radiation sterilized and ethanol-dip treatment) of sterilization used minocycline/rifampin (2:1) and minocycline/EDTA (2:1) did not alter the efficacy of the antimicrobial agents (catheter device FIG. 2 and prototype 2) or the antimicrobial device tested.

EXAMPLE 7

Long Term Antimicrobial Efficacy of Silicone-Sheathed Antimicrobial Catheter in Agar Antimicrobial catheters were prepared as demonstrated in the prototype of Example 1, prototype 2 (FIG. 2) using minocycline/rifampin (2:1) as the antimicrobial agents. The samples were embedded in agar plates inoculated with SE-5667 as outlined in Table 1. The samples were reimplanted weekly. The samples were challenged for 14 cycles (each cycle=about seven days).

Figure 8:
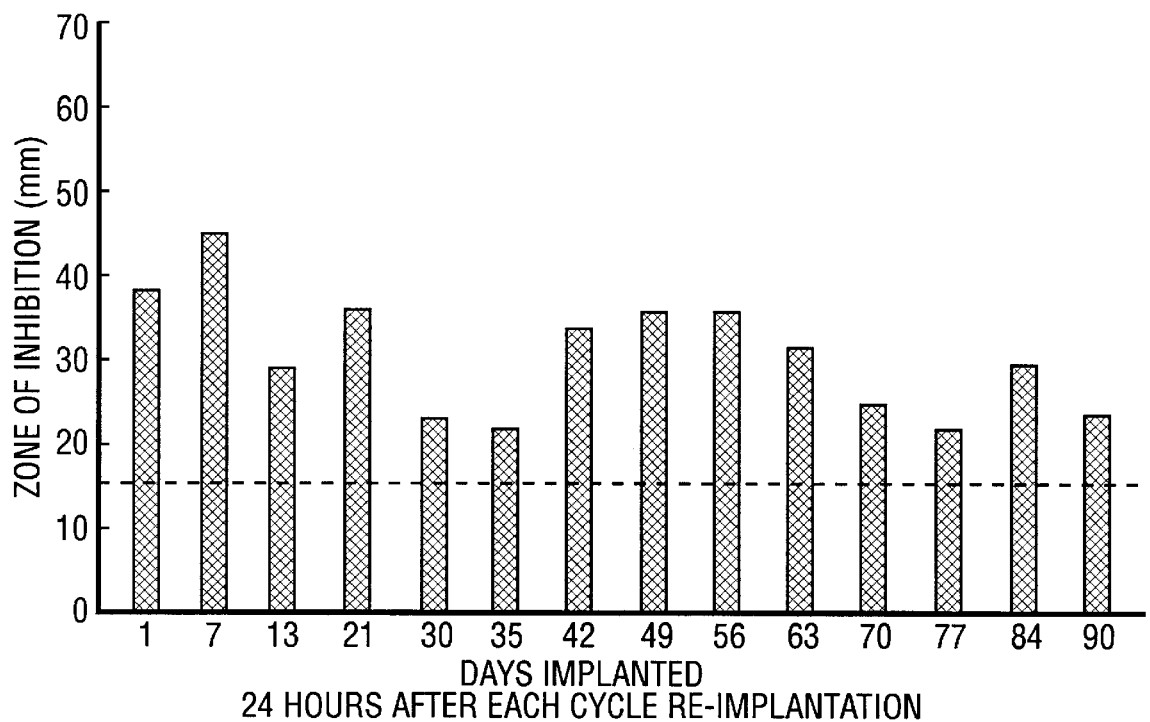
FIG. 8. efficacy of silicone sheathed antimicrobial (minocycline/rifampin; 2:1) catheters.
Figure 9:
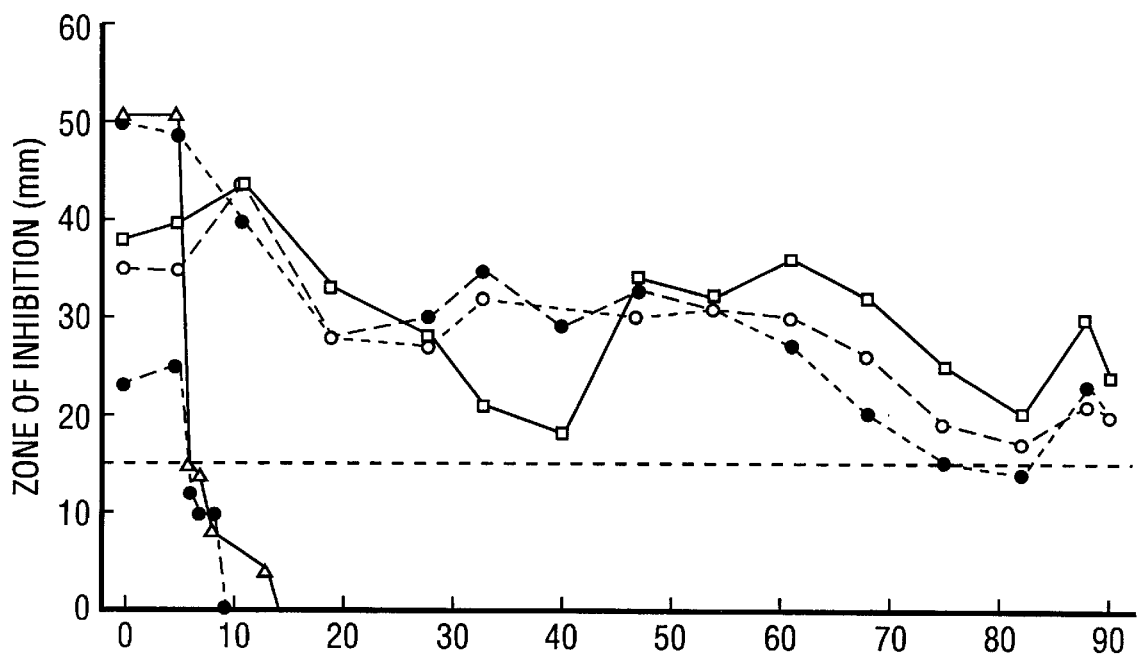
FIG. 9 shows a comparison of the long-term efficacy of 3 silicone sheathed antimicrobials to Arrow and Cook+ minocycline-coated catheters. Minocycline/Rifampin 2:1=--●--; Minocycline/Rifampin 2:1=--■--; Minocycline/EDTA 2:1=···●···; Arrow=-●-●-●-; Cook+Minocycline=--▲--.

The 24 h zones of inhibition were recorded as shown in FIG. 8. The means of the daily measurements from the 14 cycles are graphed in FIG. 9.

The silicone sheathed antimicrobial device maintained a significant antimicrobial activity, even though challenged repeatedly with reimplantation for 14 consecutive cycles. The residual antibiotic inhibitory activity of the 14 consecutive cycles persisted for at least 90 days after catheter reimplantation. Seven such residual activities are illustrated in FIG. 12.

These data demonstrate that in vivo, the efficacy of such catheters would be markedly more significant over their long term activity shown in FIG. 8 and FIG. 9, since they will not be challenged repeatedly but exert their action in one continuous period. In vivo (i.e. serum), the devices are expected to maintain a zone of inhibition around their circumference for a longer period of time than in the in vitro conditions (i.e. agar). This is supported by results obtained in serum culture, as demonstrated in Example 8 below. Furthermore, the long-term efficacy of the devices surpass the short-term antimicrobial activity of the Arrow and Cook+minocycline-coated catheters (FIG. 9).

EXAMPLE 8

Long Term Antimicrobial Efficacy of Silicone Sheathed Antimicrobial Catheters in Serum Antimicrobial catheters were prepared as demonstrated in the prototype 2, FIG. 2 using minocycline/rifampin (2:1) as the antimicrobial agents. After sterilizing the samples with ethylene oxide, the catheters were individually submerged in serum, covered and incubated at 37° C. for the specified time as described above. The samples were left incubating in the serum for 3, 7, 14, 28, 42, 56, 90 and 120 days. At each specified time the samples were removed from the serum and embedded in agar plates similar to the procedure outlined in Table 1 (step B).

Figure 10:
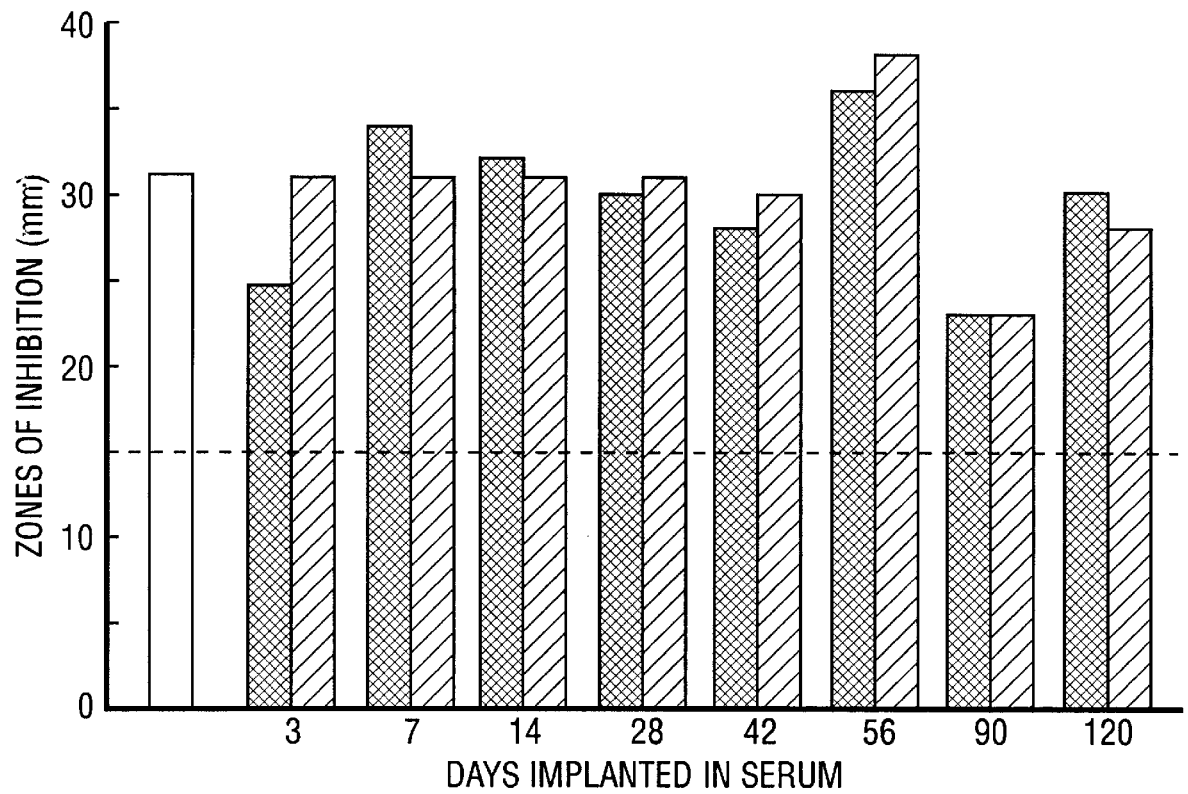
FIG. 10 shows long-term efficacy of silicone sheathed antimicrobials (minocycline/rifampin; 2:1) implanted in human serum for 120 days. Data represents 24 h zones of inhibition after each re-implantation. Pre-incubation baseline=open bar; Sample 1=double cross-hatch; Sample 2=cross-hatch.

The 24 h zones of inhibition were recorded as a measure of the efficacy of the catheters to control microbial growth. The results of this study are represented in FIG. 10. The study was carried out to 120 days, at which time the antimicrobial devices continued to demonstrate significant long-term antimicrobial activity. This activity was similar to the beginning baseline value.

REFERENCES

The following references, to the extent that they provide exemplary procedural or other details supplementary to those set forth herein, are specifically incorporated herein by reference.
1. Durand, D. B., Shaw, J P., Bush, M R., Replogle, R E., Belagaje, R and Crabtree, G R. Characterization of antigen receptor elements within the interleukin-2 enhancer. *Mol. Cell Biol.* 8:1715 (1988).
2. Owaki, H., Varma, R., Gillis, B., Bruder, T T., Rapp, U R., Davis L S., and Geppert, T D. Raf-1 is required for T cell IL-2 production. *EMBO J.* 12:4367–4373 (1992).
3. Gorman, C M., Moffat, L F., and Howard, B H. Recombinant genomes which express chloramphenicol acetyltransferase in mammalian cells. *Mol. Cell Biol.* 2:1044 (1982).
4. Wepsic et al., U.S. Pat. No. 3,598,127.
5. Laurin et al., U.S. Pat. No. 4,677,143.
6. Raad et al., U.S. Pat. No. 5,362,754.
7. Raad et al., U.S. Pat. No. 5,324,275.
8. Raad et al., U.S. Pat. No. 5,217,493.
9. Sherertz et al.. (1993) Efficacy of antibiotic-coated catheters in preventing subcutaneous *Staphylococcus aureus* infection in rabbits. *J. Infect. Dis.* 167:98–106.
10. Maki et al., Clinical trial of a novel antiseptic central venous catheter, abstr. 461, p. 176. Program abstr. 33rd Intersci. Conf. Antimicrob. Agents Chemother. American Society for Microbiology, Chicago, Ill.

It is claimed:

1. An urethral catheter comprising:
    (i) a catheter;
    (ii) an outer sheath comprising a silicone compound concentric to and surrounding said catheter; and
    (iii) a pharmacologically active agent circumferentially located between said catheter and said outer sheath, wherein said pharmacologically active agent is embedded in a jacket of hydrophobic pharmacologically active agent-permeable material,
and wherein said outer sheath is permeable to said pharmacologically active agent to allow said pharmacologically active agent to slowly diffuse through the outer sheath, and also diffuse into the lumen of the catheter.

2. A venous or arterial catheter comprising:
    (i) a catheter;
    (ii) an outer sheath comprising a silicone compound concentric to and surrounding said catheter; and
    (iii) a pharmacologically active agent circumferentially located between said catheter and said outer sheath, wherein said pharmacologically active agent is embedded in a jacket of hydrophobic pharmacologically active agent-permeable material,
and wherein said outer sheath is permeable to said pharmacologically active agent to allow said pharmacologically active ingredient to slowly diffuse through said outer sheath.

3. The catheter of claim 1 or 2, wherein said catheter is constructed from material which is nonpermeable to said pharmacologically active ingredient.

4. The catheter of claim 3, wherein said outer sheath is constructed from polysiloxane rubber.

5. The catheter of claim 4, wherein said pharmacologically active ingredient is at least one of the ingredients selected from the group consisting of chloramphenicol, fusidic acid, EDTA, minocycline and rifampin.

6. The construct of claim 5, wherein said pharmacologically active agent is chloramphenicol.

7. The construct of claim 5, wherein said pharmacologically active agent is fusidic acid.

8. A method of using an indwelling medical construct comprising the steps of:
    (i) providing an indwelling medical construct comprising:
        (a) a tube comprising a silicone compound and having a hollow inner lumen;
        (b) an outer sheath comprising a silicone compound concentric to and surrounding said tube; and
        (c) a pharmacologically active agent circumferentially located between said tube and said outer sheath, wherein said pharmacologically active agent is embedded in a jacket of hydrophobic pharmacologically active agent-permeable material, and wherein said outer sheath and hollow tube are permeable to said pharmacologically active agent to slowly diffuse through the outer sheath, and also diffuse into said lumen of said tube; and (ii) inserting said construct into a patient.

9. An indwelling medical construct comprising:

(i) an implantable medical device or a tube;

(ii) a sheath comprising a silicone compound surrounding part or all of said device or tube, said sheath being concentric to and surrounding said device or tube; and (iii) at least one pharmacologically active agent circumferentially located between said device or tube and said sheath, wherein said pharmacologically active agent is embedded in a jacket of hydrophobic pharmacologically active agent-permeable material, and wherein said sheath is permeable to said pharmacologically active agent to allow said pharmacologically active agent to slowly diffuse through said sheath.

10. The construct of claim 1, wherein said sheath and tube are constructed from polysiloxane rubber.

11. The construct of claim 1, wherein said hydrophobic pharmacologically active agent-permeable material is silicone.

12. The construct of claim 9, wherein said device or tube is adapted to be slowly permeable to said pharmacologically active agent during use.

13. The construct of claim 12, wherein said device or tube is embedded with at least one pharmacologically active agent.

14. The construct of claim 9, wherein said sheath is embedded with at least one pharmacologically active agent.

15. The construct of claim 9, wherein said device or tube is a tube.

16. The construct of claim 9, wherein said device or tube is an implantable medical device.

17. The construct of claim 16, wherein said implantable medical device is selected from the group consisting of a shunt, a peritoneal tube, a tracheotomy device, an abdominal cavity drainage tube, an angioplasty device, an implantable medical prosthesis or a device adapted to be left implanted in the body for some length of time during use.

18. The construct of claim 15, wherein said tube is a catheter.

19. The construct of any one of claims 18 or 14–17 wherein said device or tube is constructed from material which is impermeable to said pharmacologically active agent.

20. The construct of claim 18, wherein said silicone sheath is substantially coextensive with said catheter so that it encases substantially the entire length of said catheter.

21. The construct of claim 18, wherein said silicone sheath encases a portion of the length of said catheter.

22. The construct of any one of claims 18 or 14–17, wherein said pharmacologically active agent is at least one compound selected from the group consisting of: anticoagulants, wherein said anticoagulants include EGTA, EDTA, heparin, urokinase and streptokinase; antifibrin agents; antiinflammatory agents, wherein said antiinflammatory agents include steroids, nonsteroidal antiinflammatory agents and salicylates; antimicrobials, wherein said antimicrobials include antibiotics, antifungal and antiviral agents; and aztreonam.

23. The construct of claim 22, wherein said antibiotics may be selected from the group consisting of minocycline, rifampin, penicillins, cephalosporins, monobactams, carbapenems, clindamycin, chloramphenicol, tetracycline, quinolones, macrolides, sulfa antibiotics, trimethoprim, fusidic acid, gentamycin and aminoglycosides.

24. The contruct of claim 23, wherein said pharmacologically active agent is chloramphenicol.

25. The construct of claim 23, wherein said pharmacologically active agent is fusidic acid.

26. The construct of claim 23, wherein said pharmacologically active agent is at least one of the compounds selected from the group consisting of chloramphenicol, fusidic acid, EDTA, minocycline and rifampin.

27. The contruct of claim 26, wherein said pharmacologically active agent is chloramphenicol.

28. The construct of claim 26, wherein said pharmacologically active agent is fusidic acid.

29. The construct of claim 22, wherein said antiviral agents may be selected from the group consisting of acyclovir, ganciclovir, foscamet and pencyclovir.

30. The construct of claim 22, wherein said antifungal agents may be selected from the group consisting of amphotericin B, azoles, flucytosine, cilofungin and nikko Z.

31. The construct of claim 22, comprising a combination of pharmacologically active agents.

32. The construct of claim 31, wherein said combination of pharmacologically active agents is selected from the group consisting of: an antimicrobial agent and an anticoagulant; an antimicrobial agent and an antiinflammatory agent; and an antimicrobial agent, an anticoagulant and an antiinflammatory agent.

33. The construct of claim 32, wherein said combination of pharmacologically active agents is selected from the group consisting of minocycline/rifampin, minocycline/EDTA, and minocycline/aztreonam.

34. The construct of claim 33, wherein said combination of pharmacologically active agents comprises minocycline/rifampin.

* * * * *

UNITED STATES PATENT AND TRADEMARK OFFICE
CERTIFICATE OF CORRECTION

PATENT NO.    :   5,820,607

DATED         :   October 13, 1998

INVENTOR(S)   :   Robert Tcholakian and Issam Raad

It is certified that error appears in the above-identified patent and that said Letters Patent is hereby corrected as shown below:

In claim 29, column 18, line 32, delete "foscamet" and insert --fosiornet-- therefor.

Signed and Sealed this

Sixth Day of April, 1999

Attest:

Q. TODD DICKINSON

Attesting Officer

Acting Commissioner of Patents and Trademarks